United States Patent
Merlette (12)

(10) Patent No.: US 6,261,324 B1
(45) Date of Patent: Jul. 17, 2001

(54) FOOT PROSTHESIS

(75) Inventor: John B. Merlette, Sandy, UT (US)

(73) Assignee: CRP, Inc., Salt Lake City, UT (US)

( * ) Notice: Subject to any disclaimer, the term of this patent is extended or adjusted under 35 U.S.C. 154(b) by 0 days.

(21) Appl. No.: 09/320,393

(22) Filed: May 26, 1999

(51) Int. Cl.$^7$ ........................................ A61F 2/66
(52) U.S. Cl. .............................................. 623/55
(58) Field of Search ........................... 623/53–56

(56) References Cited

U.S. PATENT DOCUMENTS

| | | | |
|---|---|---|---|
| 4,822,363 | 4/1989 | Phillips | 623/27 |
| 4,959,073 | 9/1990 | Merlette | 623/55 |
| 5,219,365 | 6/1993 | Sabolich | 623/55 |
| 5,486,209 | 1/1996 | Phillips | 623/52 |
| 5,593,456 | 1/1997 | Merlette | 623/49 |
| 5,728,171 | 3/1998 | Bryant, Jr. et al. | 623/38 |
| 5,888,239 | * 11/1999 | Wellershaus et al. | 623/55 |
| 5,993,487 | * 11/1999 | Skardoutos et al. | 623/38 |

* cited by examiner

Primary Examiner—Bruce Snow
(74) Attorney, Agent, or Firm—Sheppard, Mullin, Richter & Hampton LLP; James R. Brueggemann (57) ABSTRACT

An improved foot prosthesis is disclosed which is durable in performance and inexpensive to manufacture, yet effective in accurately duplicating the feel and dynamic performance characteristics of the natural human foot. The prosthesis incorporates a single composite member having a forefoot portion beneath which is molded a unitary elastomeric sole that projects rearwardly from the composite member to define a heel. The elastomeric sole also projects laterally from the composite member so as to provide a degree of lateral stability that matches the inversion/eversion resistance of the normal human foot. In addition, a separate height adjuster and/or stiffness adjuster can be removably attached to the underside of the elastomeric sole, to enable the user to selectively adjust the prosthesis' heel height and/or stiffness.

13 Claims, 10 Drawing Sheets

FOOT PROSTHESIS

BACKGROUND OF THE INVENTION

This invention relates generally to foot prostheses and, more particularly, to foot prostheses configured to duplicate the dynamic performance characteristics of the human foot and ankle.

Significant advancements in the field of foot prostheses have been made in recent years, due largely to the development of composite materials technology. Foot prostheses incorporating fiberglass/epoxy and carbon fiber/epoxy composite materials have been developed, which closely duplicate the dynamic performance characteristics of the human foot and ankle.

One such foot prosthesis is disclosed in U.S. Pat. No. 4,959,073 issued to Merlette. The Merlette prosthesis incorporates an elongated composite main member having a leg section and a forwardly extending foot section, and it further incorporates a heel member projecting rearwardly from the underside of the main member's foot section. A high-density polyurethane elastomer is disposed between the heel member and the main member's foot section, to permanently attach the two members together and to provide limited cushioning. The upper end of the main member's leg section supports an amputation socket for receiving the amputee's residual limb, and a crepe sole can be attached to the underside of the heel member. A foam foot shell or cosmesis can be placed over the composite members, to provide the prosthesis with an appearance of a normal human foot.

The Merlette foot prosthesis described briefly above has enjoyed substantial commercial success. Nevertheless, it is believed that the Merlette prosthesis can be improved upon by simplifying its manufacture, thus reducing both material and labor costs, and by minimizing the possibility of component failure.

Users of foot prostheses of this kind typically will desire to use the prosthesis while wearing a variety of shoes having heels of different heights. One drawback to prior foot prostheses is that they typically have been configured to have a fixed heel height. They typically have not been configured to provide for a convenient adjustment of their heel height, to allow the user to use the prosthesis with a variety of shoes.

Users of foot prostheses of this kind typically also will desire to use the prosthesis in a variety of physical activities. Some of these activities will be best engaged in using a prosthesis having relatively high stiffness, while others will be best engaged in using a prosthesis having relatively low stiffness, or high compliance. Despite this desire, foot prostheses generally have not been configured to provide for a convenient adjustment of their stiffnesses.

It should therefore be appreciated that there exists a need for a foot prosthesis that can be manufactured more economically and that is configured to facilitate a convenient adjustment of its heel height and its stiffness. The present invention fulfills this need and provides further related advantages.

SUMMARY OF THE INVENTION

The present invention is embodied in an improved foot prosthesis, and in a method for making it, which can be manufactured more economically and which is configured to facilitate a convenient adjustment of its heel height and/or its stiffness. The foot prosthesis includes an elongated monolithic composite member having a forwardly extending forefoot section, and further includes a high-density elastomeric sole molded to the underside of the forefoot section of the monolithic composite member, the elastomeric sole including a heel section projecting rearwardly from the forefoot section, to define a heel, and further including lateral and medial sections projecting laterally from the forefoot section. An elastomeric cosmesis having the general shape of a human foot can conformably envelope the elastomeric sole.

In more detailed features of the invention, the elongated monolithic composite member has a substantially uniform width, and it is formed of a carbon fiber composite material. In addition, the elastomeric sole has a peripheral shape similar to that of a normal human foot, and it preferably is formed of a high-density polyurethane. The elastomeric sole preferably incorporates lateral and medial sections having a maximum transverse width about three times greater than the substantially uniform width of the composite member. In some embodiments, the monolithic composite member incorporates a generally vertically oriented pylon section that projects above a rearward portion of its forefoot section. An elastomeric coating can be disposed on this pylon section, to facilitate mechanical coupling to an amputation socket.

In a separate and independent feature of the invention, the foot prosthesis further includes a sole plate configured to have a peripheral shape substantially the same as the peripheral shape of the elastomeric sole and further configured to be releasably securable to the underside of the elastomeric sole, so as to modify a predetermined parameter (e.g., stiffness and/or heel height) of the foot prosthesis' physical characteristic.

In one embodiment, the sole plate includes an elongated monolithic composite member extending along substantially the entire length of the sole plate, and further includes a high-density elastomeric material molded under or around the elongated monolithic composite member. In this embodiment, the sole plate, when attached to the underside of the elastomeric sole, adjusts the stiffness of the foot prosthesis. In another embodiment, the sole plate is thicker in its rearward portion than in its forward portion, so as to adjust the foot prosthesis' heel height.

The sole plate can be releasably attached to the elastomeric sole by configuring the upper side of the sole plate and the underside of the elastomeric sole to incorporate complementary relief patterns. This relief pattern is configured to prevent relative movement or shifting between the two components, either medial to lateral or anterior to posterior. One suitable pattern is a waffle pattern.

In another separate and independent feature of the invention, the foot prosthesis is made by 1) forming a laminate of high-strength composite material, 2) making a series of parallel cuts through the laminate, to form a plurality of elongated, monolithic strips of composite material having substantially uniform widths, and 3) molding a high-density elastomeric sole to the underside of each elongated strip of composite material. Each such elastomeric sole includes a heel section projecting rearwardly from the composite member, and it further includes lateral and medial sections projecting laterally from the composite member. Finally, a low-density foam cosmesis having the general shape of a human foot is conformably placed or molded around each of the elastomeric soles, to produce a plurality of foot prostheses.

In more detailed features of the invention, the laminate of high-strength composite material has a thickness that varies from one edge to an opposite edge. In addition, it is molded into a predetermined shape, such that each of the plurality of elongated strips of composite material will have a generally vertically oriented pylon section and a generally horizontally oriented forefoot section. The composite strips are thickest in the ankle section, where the pylon section transitions to the forefoot section.

Other features and advantages of the present invention should become apparent from the following description of the preferred embodiments, taken in conjunction with the exemplary drawings, which illustrate the principles of the invention.

DESCRIPTION OF THE PREFERRED EMBODIMENTS

With reference now to the illustrative drawings, and particularly to FIGS. 1–5, there is shown a first embodiment of a foot prosthesis 100 in accordance with the invention, the prosthesis incorporating a single elongated composite member 102 and an underlying molded elastomeric sole 104. The prosthesis duplicates the dynamic performance characteristics of the normal human foot, yet it is of simple construction and can be manufactured relatively inexpensively.

The composite member 102 preferably is formed of a conventional carbon fiber/epoxy material, and it has a rectangular cross-section along its entire length, with a generally vertically oriented pylon section 106 at its upper end and a generally horizontally oriented forefoot section 108 at its lower end. Below the pylon section, the composite member curves smoothly rearwardly and then forwardly through a gooseneck ankle section 110, to become the forefoot section. The width of the composite member is substantially uniform along its entire length, except at the tip of its forefoot section, which is rounded or otherwise contoured to match the toe shape of the sole or foot shell. The thickness of the composite member is uniform through its pylon section before increasing through its ankle section and then decreasing through its forefoot section to a minimum thickness at its remote tip.

Figure 3:
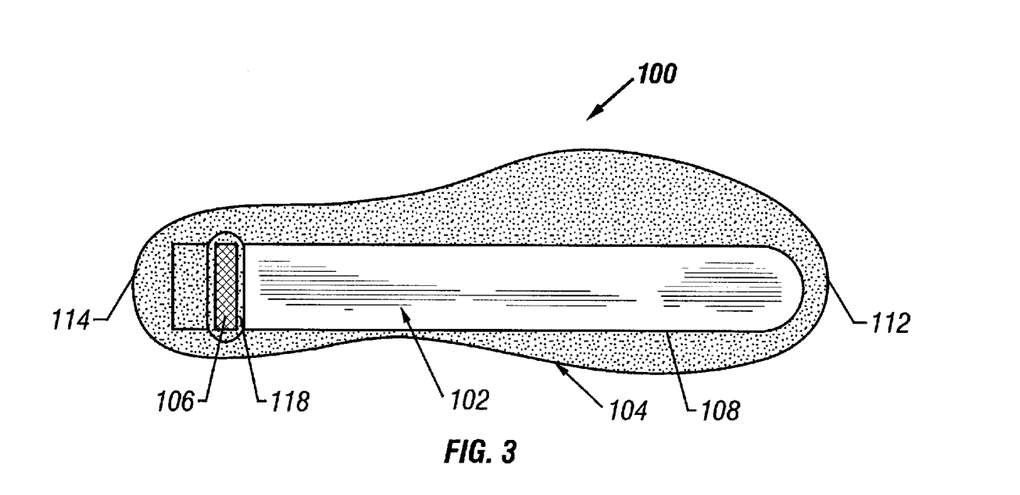
FIG. 3 is a top plan view of the foot prosthesis of FIG. 1.
Figure 4:
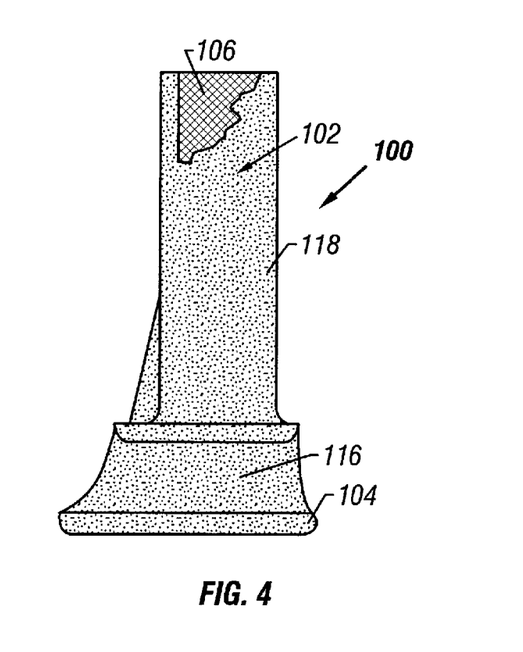
FIG. 4 is a rear elevational view of the foot prosthesis of FIG. 1.

The elastomeric sole 104 is formed of a high-density polyurethane material, and it is molded beneath the entire forefoot section 108 and the lower portion of the gooseneck ankle section 110 of the composite member 102. As best shown in FIG. 3, the elastomeric sole's outer periphery is generally the same as that of a natural human foot, with a maximum width about three times greater than the width of the composite member. It will be appreciated that other relative widths alternatively could be used. The elastomeric sole projects forwardly slightly from the tip of the forefoot section, to define a resilient toe 112, and it projects a substantial distance from the rearward extent of the ankle section, to define a resilient heel 114.

Figure 2:
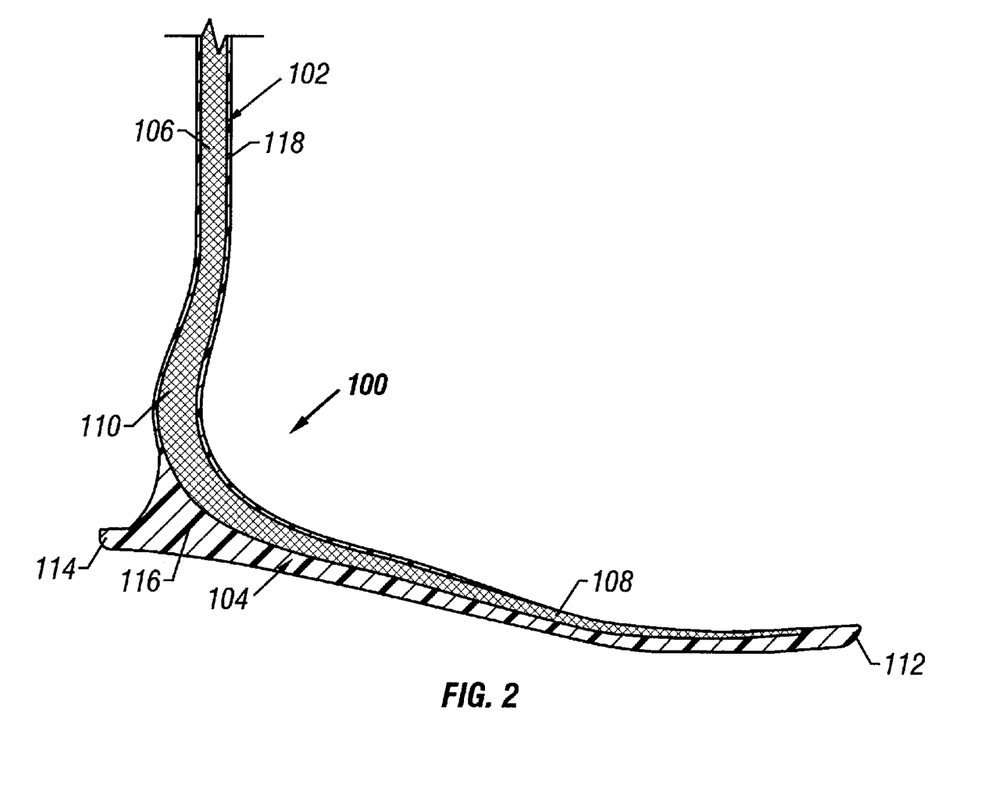
FIG. 2 is a side sectional view of the foot prosthesis of FIG. 1.

The elastomeric sole 102 has a substantially uniform thickness of about 5 mm in the region beneath the composite member's forefoot section 108, but its thickness increases substantially in the region beneath the curvilinear gooseneck ankle section 110, so as to define a projecting heel 116. The upper portion of the ankle section and the pylon section 106 preferably are encapsulated with the same material as the elastomeric sole, as indicated by the reference numeral 118. This facilitates a reliable connection to an amputation socket (not shown) at the upper end of the pylon section.

Figure 1:
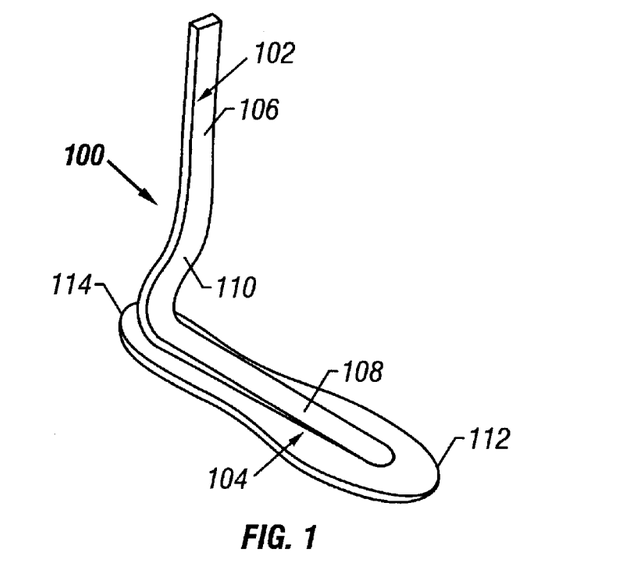
FIG. 1 is a perspective view of a first embodiment of a foot prosthesis in accordance with the invention, the embodiment including a single composite member and a polyurethane layer molded beneath it.

During use of the foot prosthesis 100, the user's weight is principally borne by the composite member 102 and transferred through the elastomeric sole 104 to the ground. The impact of heel strike is cushioned by the heel 116 of the elastomeric sole, and as the user rocks forward during a step, the user's weight flexes the ankle section 110 and the forefoot section 108. The energy absorbed during this flexing largely will be returned to the user during toe-off. Compression of the elastomeric sole and flexing of the composite member act to greatly soften the impact with the ground and generally duplicate the feel and dynamic performance characteristics of the natural human foot during walking.

The elastomeric sole 104 also enables the foot prosthesis 100 to duplicate the feel and dynamic performance characteristics of the natural human foot in resisting inversion and eversion. Specifically, the portions of the elastomeric sole that project laterally from the composite member 102, especially at its widest point, resist pronation and supination to a degree similar to that provided by the normal human foot. Thus, if during walking, a lateral or medial side edge of the elastomeric sole overlays a small pebble, that portion of the elastomeric sole will yield upwardly and substantially diminished torque will be transferred to the composite member.

Figure 5:
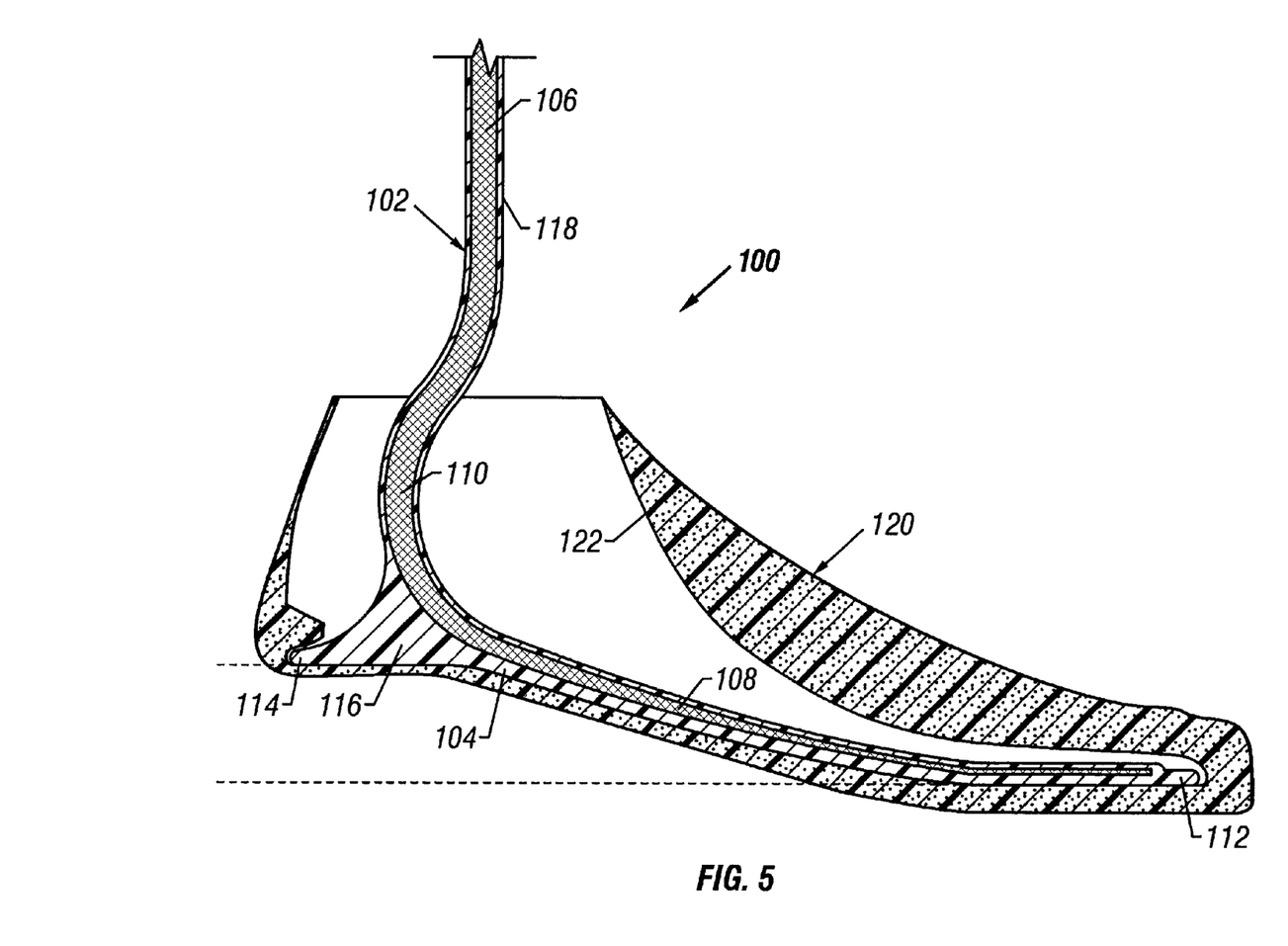
FIG. 5 is a side sectional view of the foot prosthesis of FIG. 1, positioned within a foam cosmesis.

As shown in FIG. 5, the foot prosthesis 100 further incorporates a conventional foam foot shell, or cosmesis 120. The cosmesis, which has the outward appearance of a normal human foot, incorporates an internal cavity 122 that is sized and configured to conformably receive the forefoot portion of the prosthesis' composite member 102 and elastomeric sole 104.

A second embodiment of a foot prosthesis 200 in accordance with the invention is depicted in FIGS. 6–9. In this embodiment, components of the prosthesis having corresponding components in the first embodiment are identified by corresponding reference numerals in the 200's. The prosthesis 200 is substantially identical to the prosthesis 100 of FIGS. 1–5, except that it incorporates an elastomeric sole 204 that is substantially thicker than is the elastomeric sole 104 of the prosthesis 100. A substantially larger heel 216 thereby is defined.

The elastomeric sole 204 of the foot prosthesis 200 (FIGS. 6–9) is generally similar to the elastomeric sole 104 of the prosthesis 100 (FIGS. 1–5), in the forward portions of the prostheses' forefoot portions. The prostheses therefore provide similar dynamic performances at toe-off and in resisting inversion and eversion.

Figure 6:
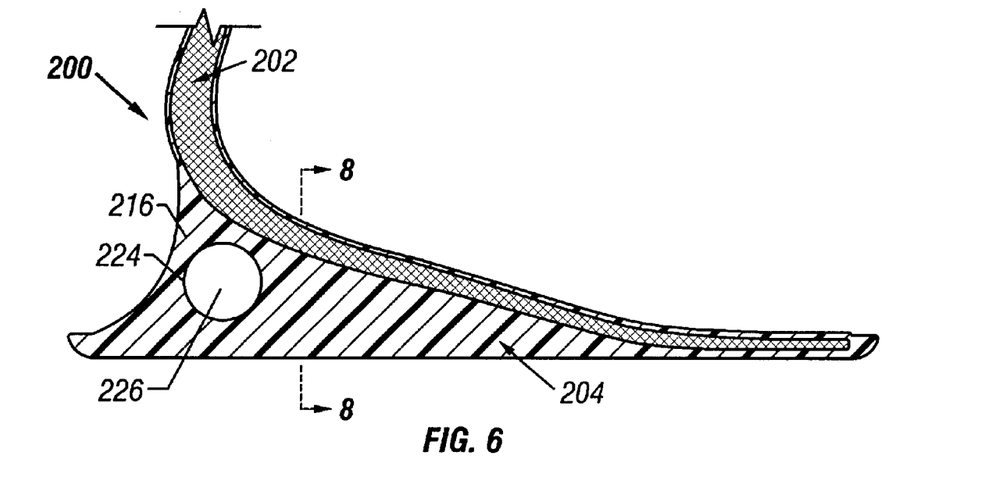
FIG. 6 is a side sectional view of a second embodiment of a foot prosthesis in accordance with the invention, this embodiment differing from the embodiment of FIG. 1 in that its molded polyurethane layer has a reduced heel height.
Figure 7:
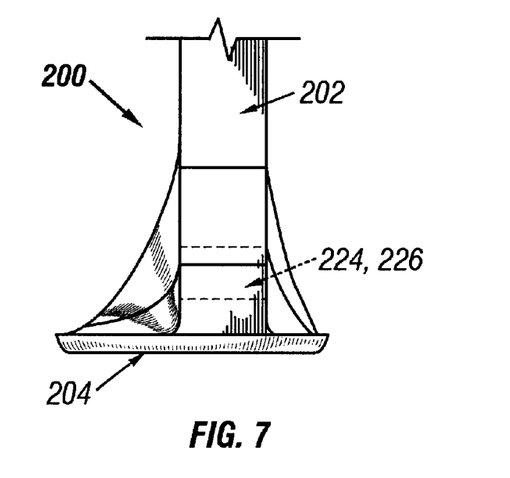
FIG. 7 is a rear elevational view of the foot prosthesis of FIG. 6.
Figure 8:
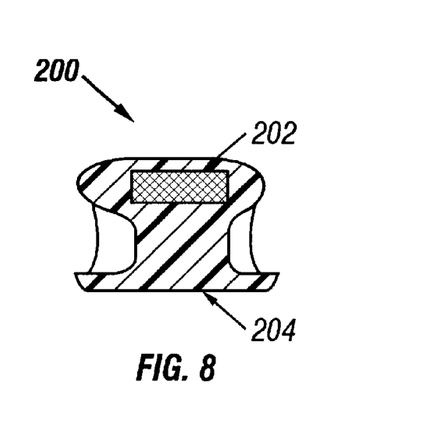
FIG. 8 is a cross-sectional view of the foot prosthesis of FIG. 6, taken substantially in the direction of the arrows 8—8 in FIG. 6.

A transverse, circular through-hole 224 be formed in the enlarged heel 216 of the prosthesis 200, for receiving a removable cylindrical plug 226. The hole and plug preferably have circular cross-sections. When the plug is present in the hole, the heel is relatively hard, whereas when the plug is removed, the heel is relatively soft. This enables limited adjustments to be made to the amount of cushioning provided by the prosthesis on heel strike.

Figures 9, 10:
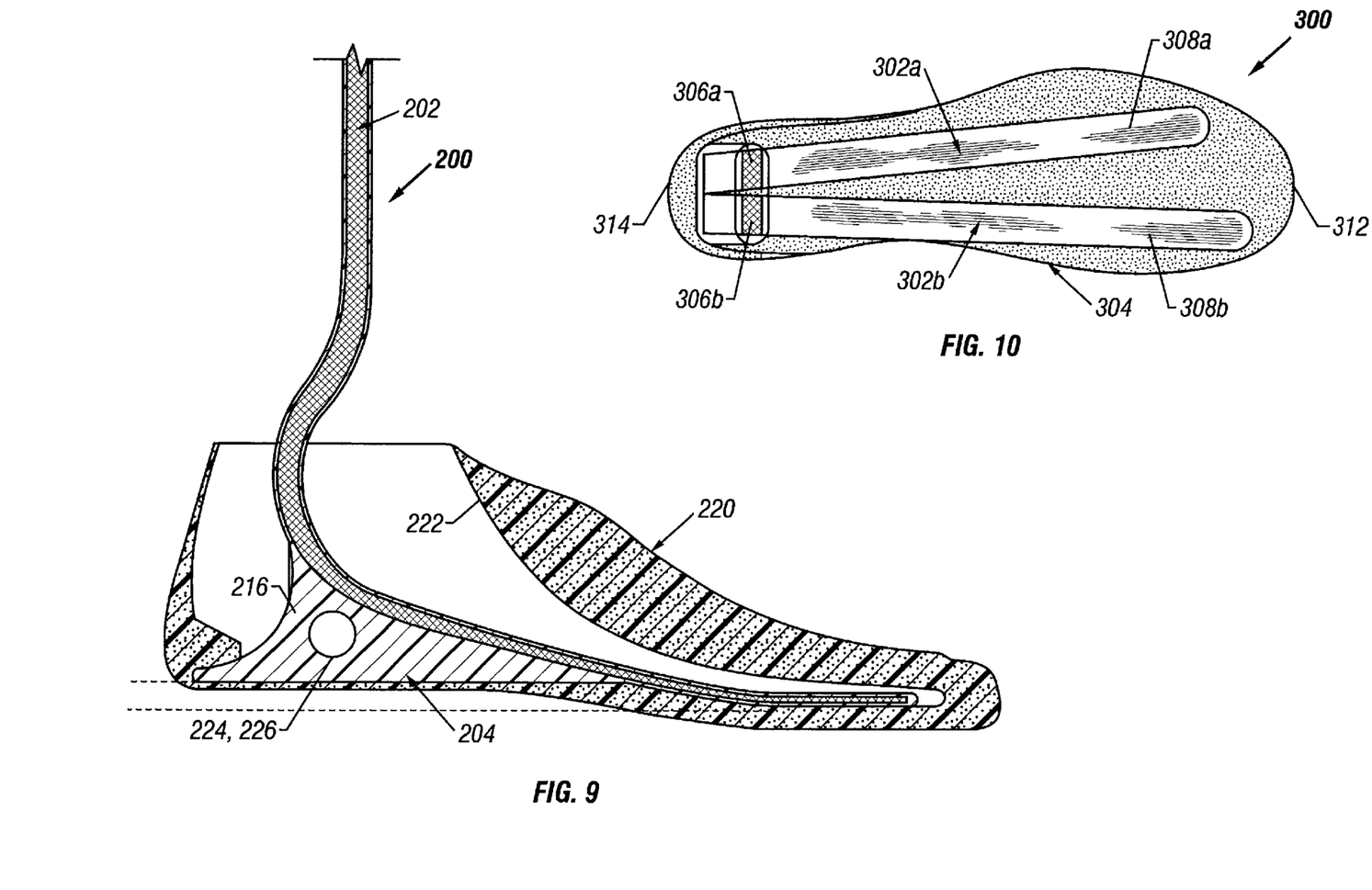
FIG. 9 is a side sectional view of the foot prosthesis of FIG. 6, positioned within a foam cosmesis.
FIG. 10 is a top plan view of a third embodiment of a foot prosthesis in accordance with the invention, this embodiment differing from the first and second embodiments in that the composite member is bifurcated into two components, which are parallel with each other in the region of the pylon section, but which diverge apart in the forefoot section.

The foot prosthesis 200 further incorporates a conventional foam foot shell, or cosmesis 220, as shown in FIG. 9. The cosmesis has an internal cavity 222 sized and configured to conformably receive the forefoot portion of the composite member 202 and the elastomeric sole 204.

In a modification to the foot prosthesis 200 (not shown in the drawings), a plurality of downwardly facing recesses may be formed in the heel 216. These recesses will reduce the weight of the prosthesis, while providing a softer dynamic feel upon heel strike.

A third embodiment of a foot prosthesis 300 in accordance with the invention is depicted in FIG. 10. It is similar to the prosthesis 200 of FIGS. 6–9, except that it incorporates a bifurcated composite member. In particular, the composite member is split into two segments 302a and 302b of substantially identical widths and cross-sectional shapes. These two segments include pylon sections 306a and 306b, which are arranged in parallel relationship with each other, and forefoot sections 308a and 308b, which diverge from each other. The prosthesis 300 provides somewhat improved inversion/eversion and lateral stability as compared to the prosthesis 200, but its dynamic performance at toe-off is somewhat softer.

A fourth embodiment of a foot prosthesis 400 in accordance with the invention is depicted in FIGS. 11–14. The prosthesis 400 is similar to the prostheses 100 (FIGS. 1–5) and 200 (FIGS. 6–9), except that the composite member 402 has a different shape in the region of its pylon section 406 and its ankle section 410, as is described below. In addition, the composite member preferably is formed of a conventional fiberglass/epoxy composite (FRP) material. The composite member has a substantially uniform width in its forefoot section 408, and this width is about one-third to one-half the maximum width of the prosthesis' elastomeric sole 404.

Figure 11:
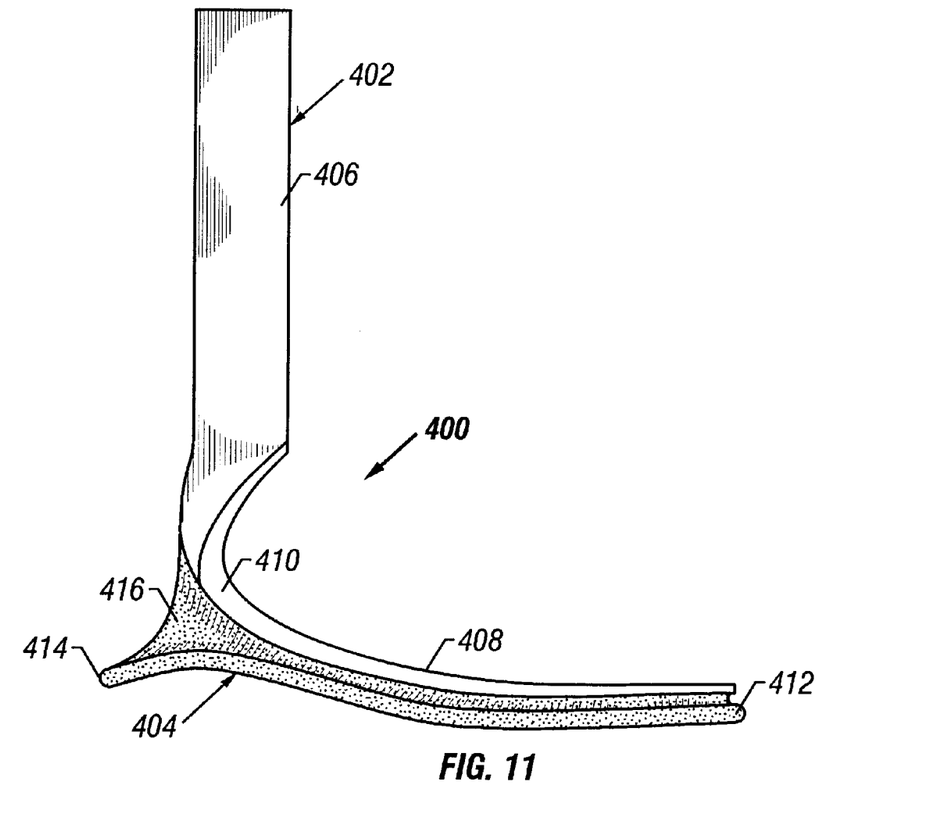
FIG. 11 is a side elevational view of a fourth embodiment of a foot prosthesis in accordance with the invention, this embodiment incorporating a single composite member and a polyurethane layer molded beneath it.
Figure 12:
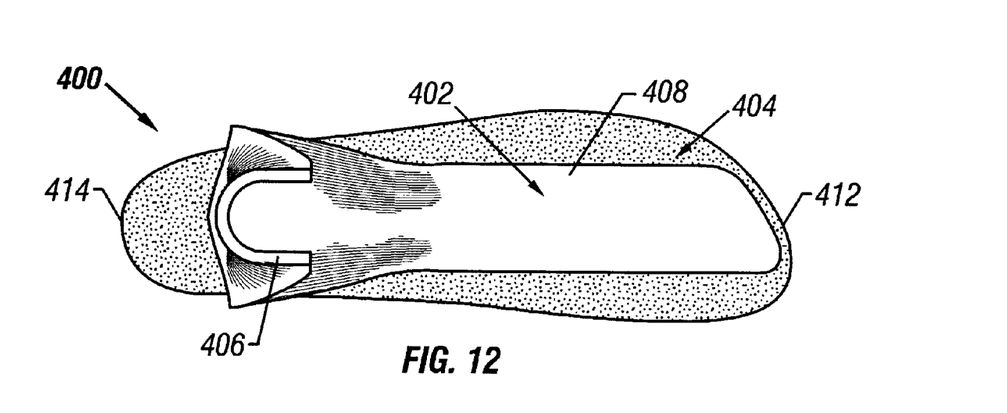
FIG. 12 is a top plan view of the foot prosthesis of FIG. 11.

The pylon section 406 of the composite member 402 has a generally U-shaped cross-section, which renders it substantially resistant to flexing about all axes other than a vertical axis. In addition, the ankle section 410 transitions from a U-shaped cross-section at its upper end to a rectangular cross-section and then bends smoothly forwardly to become the forefoot section 408. The wall thickness of the composite member is uniform in its pylon section 406, and it increases to a maximum in the ankle section 410 before tapering to the tip of the forefoot section 408.

Figure 13:
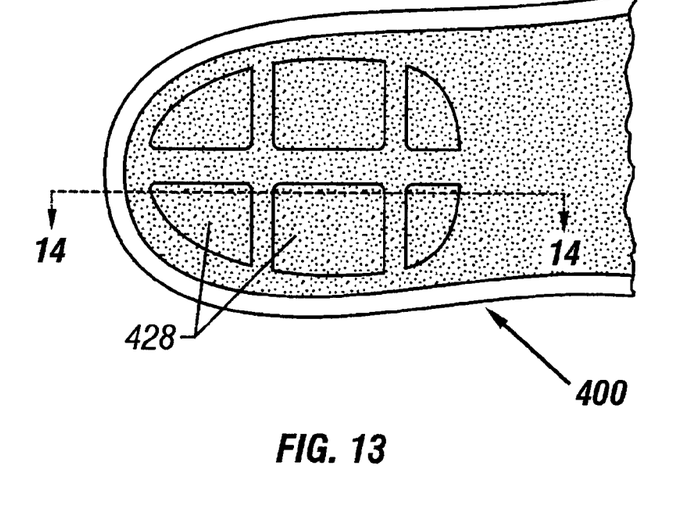
FIG. 13 is a bottom plan view of the heel portion of the foot prosthesis of FIG. 11, showing cutout portions to reduce its mass.
Figure 14:
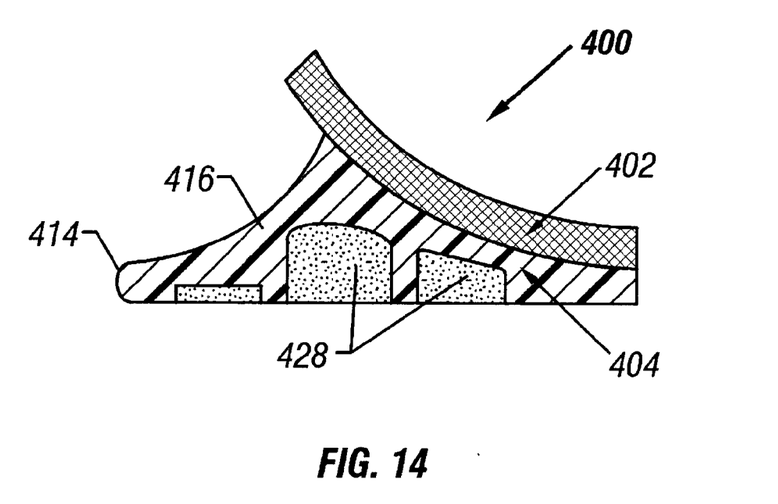
FIG. 14 is a fragmentary sectional view of the foot prosthesis of FIG. 11, the view being taken substantially in the direction of the arrows 14—14 in FIG. 13.

As shown in FIGS. 13 and 14, an optional array of recesses 428 may be formed in the underside of the heel 416 defined by the prosthesis' elastomeric sole 404. These recesses function to lighten the prosthesis' weight, and they provide a softer, more compliant feel upon heel strike.

The foot prosthesis 400 thus is optimized for use in relatively sedentary activities, e.g., slow walking. It does not provide the same degree of energy return as is provided by the foot prostheses 100 and 200. Nevertheless, like the prostheses 100 and 200, the prosthesis 400 is relatively inexpensive to manufacture and it accurately duplicates the feel and dynamic performance characteristics of the normal human foot, especially in the area of lateral stability, i.e., inversion and eversion.

Figure 15:
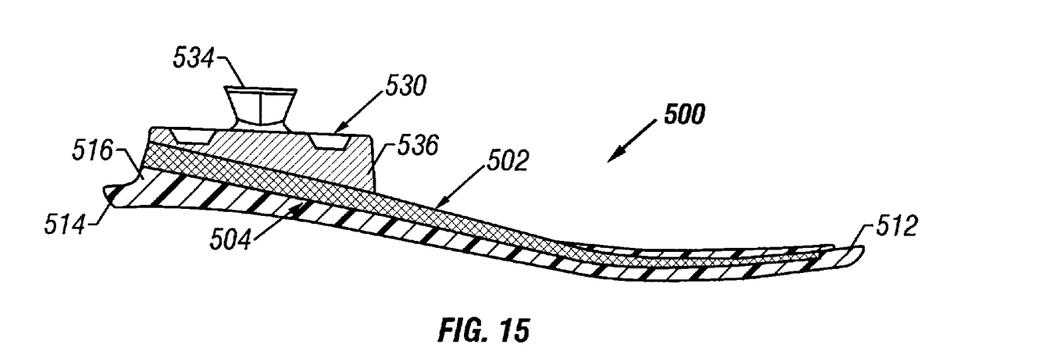
FIG. 15 is a side elevational view of a fifth embodiment of a foot prosthesis in accordance with the invention, this embodiment being of a Symes-type configuration.
Figure 16:
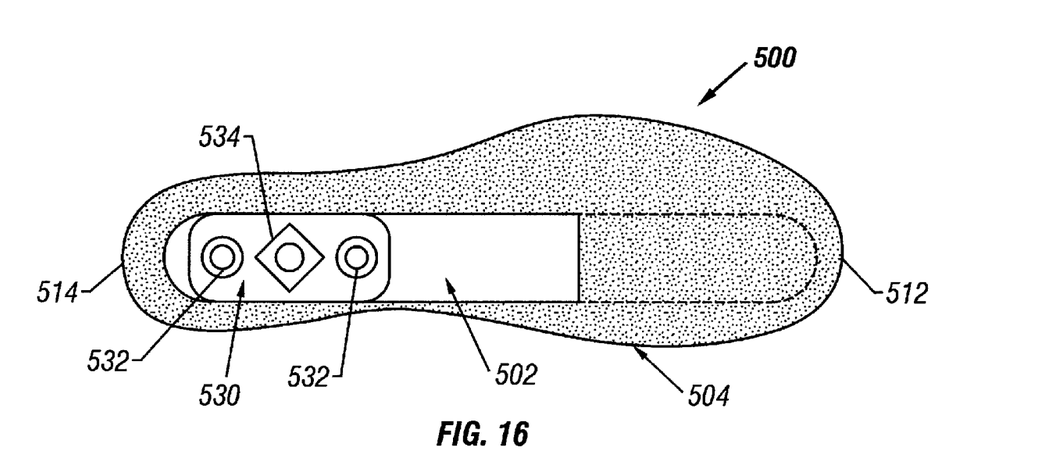
FIG. 16 is a top plan view of the foot prosthesis of FIG. 15.

A fifth embodiment of a foot prosthesis 500 in accordance with the invention is depicted in FIGS. 15–16. This prosthesis has a so-called Symes-type configuration, which is intended for use by amputees having legs amputated at or near the ankle.

Like the foot prostheses described above, the foot prosthesis 500 includes a single composite member 502 of substantially constant width, with an elastomeric sole 504 molded beneath the composite member. In the prosthesis 500, however, the composite member eliminates the pylon and ankle sections and, instead, incorporates only a generally straight foot section, or keel.

An attachment device 530 is secured by suitable fastening means, (e.g., screws 532), to the upper side of the composite keel 502, at its rearward end. Alternatively, an adhesive attachment could be used. The attachment device incorporates an undercut post 534, of conventional design, for receiving either an amputation socket or a separate pylon (not shown). A plastic or metallic wedge 536 may be positioned between the composite member and the attachment device, so that the attachment device has the proper angular orientation for the socket or pylon.

The maximum width of the elastomeric sole 504 preferably is about two to three times the width of the keel 502. The prosthesis 500 thereby accurately duplicates the feel and dynamic performance characteristics of the normal human foot, especially in the area of lateral stability, i.e., inversion and eversion.

Figure 17:
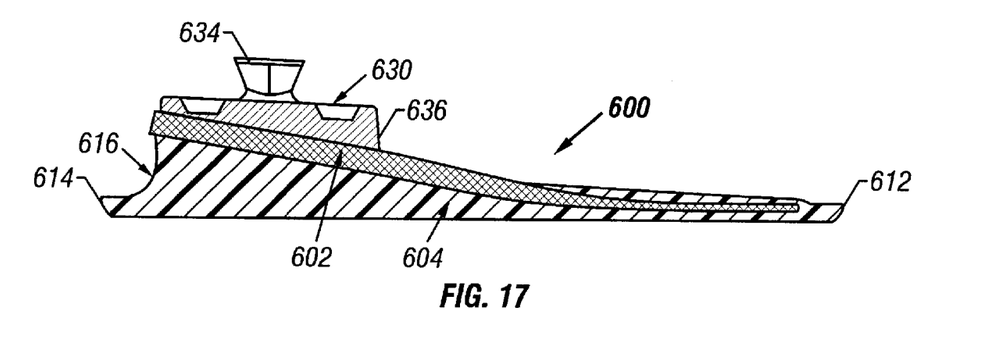
FIG. 17 is a side elevational view of a sixth embodiment of a foot prosthesis in accordance with the invention, this embodiment also being of a Symes-type configuration, but with a thicker polyurethane layer that provides a reduced heel height.

A sixth embodiment of a foot prosthesis 600 in accordance with the invention is depicted in FIGS. 17. Like the prosthesis 500 of FIGS. 15–16, the prosthesis 600 has a Symes-type configuration. However, it has a substantially thicker heel 616, giving it a lower functional heel height. The prosthesis 600 has a configuration in plan identical to that of the prosthesis 500.

Figure 18:
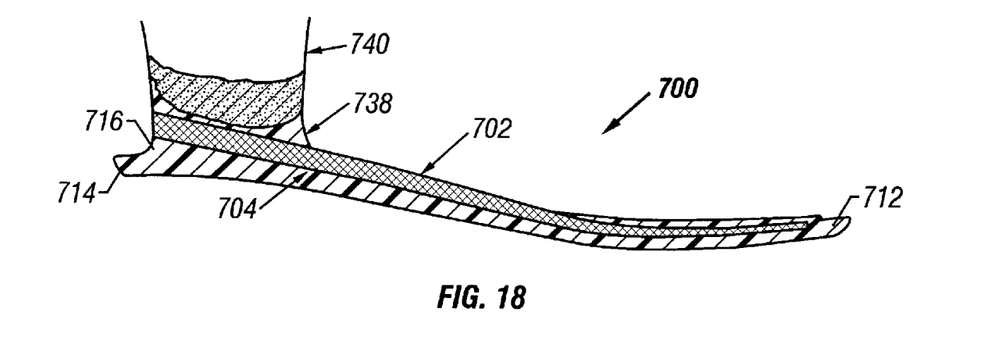
FIG. 18 is a side elevational view of a seventh embodiment of a foot prosthesis in accordance with the invention, this embodiment being of a Chopart-type configuration.
Figure 19:
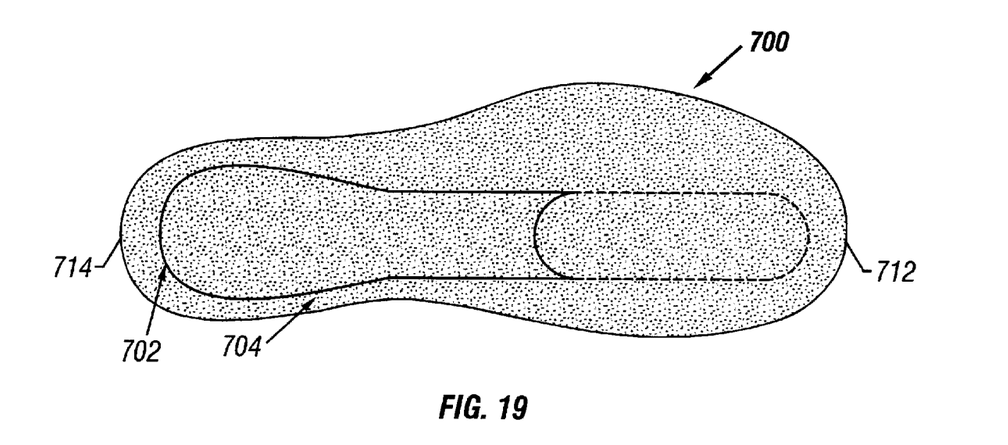
FIG. 19 is a top plan view of the foot prosthesis of FIG. 18.

A seventh embodiment of a foot prosthesis 700 in accordance with the invention is depicted in FIGS. 18–19. This prosthesis has a so-called Chopart configuration, which is intended for use by amputees having only the front portion of their foot amputated.

The prosthesis 700 is similar to the prosthesis 500 of FIGS. 15–16, except that it eliminates the attachment device. In its place is a polyurethane block 738 for making a direct bond to an amputation socket 740. The single composite member, or keel 708, may be widened or otherwise enlarged at its rearward end, to better distribute the user's weight over the prosthesis.

As is the case with the prostheses described above, the maximum width of the elastomeric sole 704 is about two to three times the width of the keel 708 in the forefoot section. The prosthesis 700 thereby accurately duplicates the feel and dynamic performance characteristics of the normal human foot, especially in the area of lateral stability, i.e., inversion and eversion.

Figure 20:
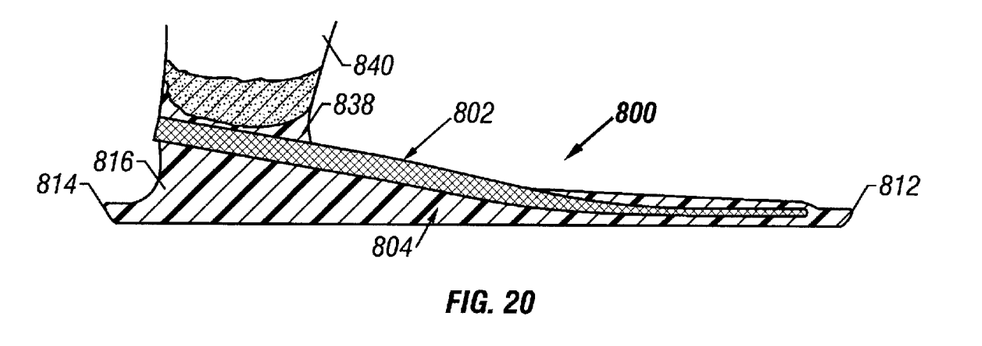
FIG. 20 is a side elevational view of an eighth embodiment of a foot prosthesis in accordance with the invention, this embodiment also being of a Chopart-type configuration, but with a thicker polyurethane layer that provides a lower heel height.

An eighth embodiment of a foot prosthesis 800 in accordance with the invention is depicted in FIGS. 20. Like the prosthesis 700 of FIGS. 18–19, the prosthesis 800 has a Chopart-type configuration. However, it has a substantially thicker heel 816, giving it a lower functional heel height. The prosthesis 800 has a configuration in plan identical to that of the prosthesis 700.

It will be appreciated that all of the foot prostheses described above have fixed heel heights and fixed stiffnesses in their forefoot sections. Each prosthesis therefore is not optimally used with a variety of shoes and in a variety of physical activities. This deficiency generally has been overcome in the past by the user maintaining an inventory of two or more separate prostheses and selecting the particular prosthesis depending on the use to be made.

Figure 21:
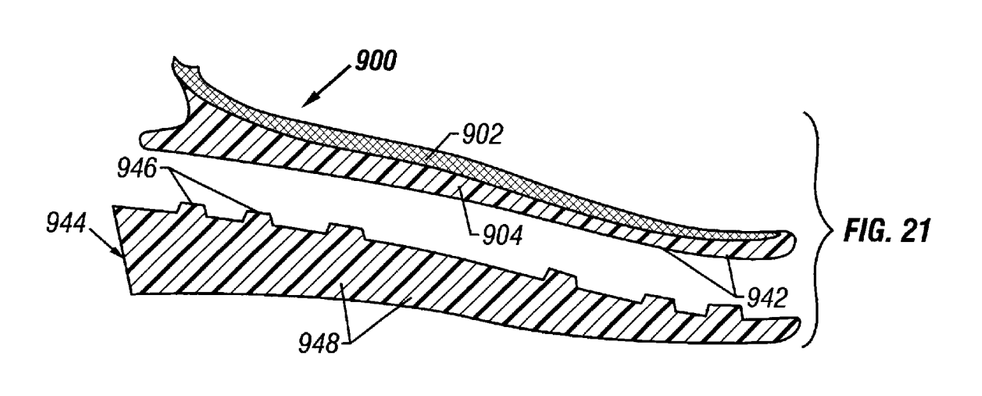
FIG. 21 is a side cross-sectional view of an embodiment of a foot prosthesis in accordance with the invention, which incorporates a height adjuster configured that can be selectively attached to the underside of the prosthesis' elastomeric sole, to adjust the prosthesis' heel height.

In a separate and independent feature of the invention, and with reference to FIG. 21, this deficiency of the prior art is overcome by configuring the underside of the prosthesis' elastomeric sole 904 to incorporate an array of recesses 942 and by providing a separate height adjuster 944 having an array of lugs 946 configured to be conformably engageable with the sole's array of recesses. The array of recesses may have the appearance of a waffle pattern. The height adjuster has a peripheral shape the same as that of the sole, and it is substantially thicker in its heel region as compared to its toe region. When a lower heel height is desired, the user simply positions the height adjuster beneath the sole, such that the lugs are conformably received by the recesses.

The height adjuster 944 preferably is molded of a suitable high-density polyurethane material, preferably the same as the material that comprises the elastomeric sole 904. The relaxed contour of the height adjuster's upper side matches that of the sole's underside. An array of recesses 948 may be formed in the height adjuster's underside, to reduce weight and to increase compliance. Of course, a set of several height adjusters 944 may be provided, each height adjuster having an array of lugs 946 but a different heel height, whereby the user can select from any of a number of desired heel heights.

Figure 22:
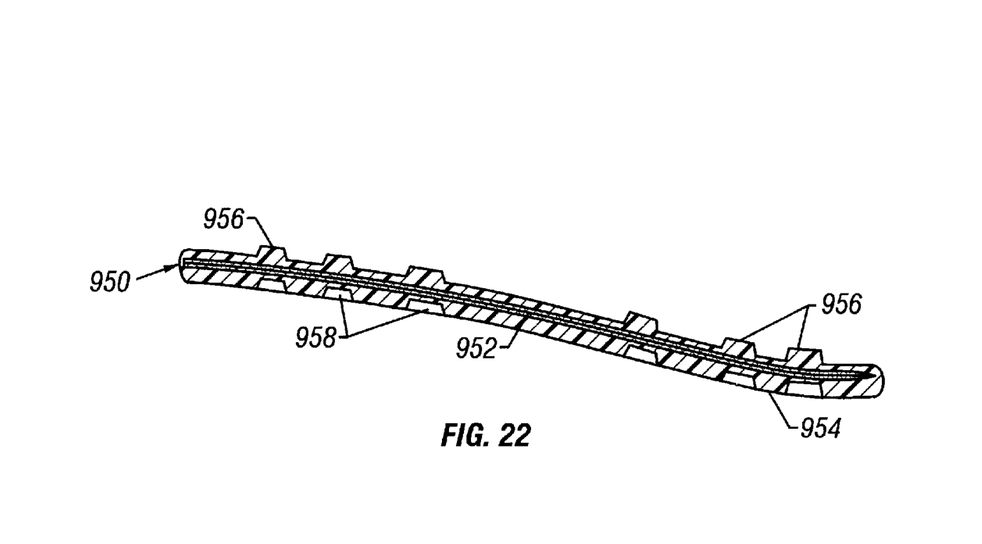
FIG. 22 is a side cross-sectional view of a sole plate that can be selectively attached to the underside of the elastomeric sole of the foot prosthesis of FIG. 21, to adjust the prosthesis' stiffness.

In another separate and independent feature of the invention, and as shown in FIG. 22, the foot prosthesis' stiffness can be modified by providing a separate stiffness adjuster 950 configured to be releasably attached to the underside of the prosthesis' elastomeric sole 904, much like the height adjuster 944 described above. In particular, the stiffness adjuster includes a composite member 952 molded within an elastomeric shell 954. The composite member may be formed of a suitable carbon fiber/epoxy (FRP) material, of selectable thickness and shape. The elastomeric shell may be formed of a high-density polyurethane, and it preferably is molded over, and encapsulates, the composite member.

The stiffness adjuster 950 preferably is attached to the underside of the prosthesis' elastomeric sole 904 in the same manner as is the height adjuster 944, described above. Specifically, an array of molded, polyurethane lugs 956 is formed in the adjuster's upper side, configured to be conformably engageable with the sole's array of recesses 942. The stiffness adjuster has a peripheral shape the same as that of the sole, and it has a substantially uniform thickness along its length. When a stiffer prosthesis is desired, e.g., when the user is engaging in a relatively vigorous activity, the user simply positions the stiffness adjuster beneath the sole, such that the lugs are conformably received by the recesses.

The relaxed contour of the upper side of the stiffness adjuster 950 matches that of the underside of the elastomeric sole 904. Of course, a set of several stiffness adjusters may be provided, each stiffness adjuster having an array of lugs 956 but a different degree of stiffness, whereby the user can select from any of a number of desired stiffnesses. Different degrees of stiffness can be provided by using a different number of plies or by using different fiber orientations in the plies. Alternatively, different degrees of stiffness can be provided by varying the hardness (durometer) of the encapsulating polyurethane shell.

Alternatively, not shown in the drawings, the stiffness adjuster can be configured such that the composite member extends over only the forefoot section or only the heel section. In either case, the encapsulating elastomeric shell would have a length the same as that of the elastomeric sole 904.

In addition, an array of recesses 958 may be formed in the stiffness adjuster's underside, to reduce weight. By configuring this array of recesses 958 to be the same as the array of recesses 942 formed in the underside of the elastomeric sole 904, a supplementary height adjuster 944 can be attached, as well. This allows the user to selectively adjust both the prosthesis' stiffness and the prosthesis' heel height, simultaneously.

Although the height adjuster 944 (and/or the stiffness adjuster 950) is releasably attached to the elastomeric sole 904 using mating arrays of lugs 946 (or 956) and recesses 942, it will be appreciated that alternative means of releasable attachment could be used as well. Preferably, the attachment can be made and released without the need for separate tools.

It should be appreciated from the foregoing description that the present invention provides an improved foot prosthesis that is durable in performance and inexpensive to manufacture, yet effective in accurately duplicating the feel and dynamic performance characteristics of the natural human foot. The prosthesis incorporates a single composite member having a forefoot portion beneath which is molded a unitary elastomeric sole that projects rearwardly from the composite member to define a heel. The elastomeric sole also projects laterally from the composite member so as to provide a degree of lateral stability that matches the inversion/eversion resistance of the normal human foot. In addition, a separate height adjuster and/or stiffness adjuster can be removably attached to the underside of the elastomeric sole, to enable the user to selectively adjust the prosthesis' heel height and/or stiffness.

Although the invention has been described in detail with reference to the presently preferred embodiments, those of ordinary skill in the art will appreciate that various modifications can be made without departing from the invention. Accordingly, the invention is defined only by the following claims.

I claim:

1. A foot prosthesis comprising:
    an elongated monolithic composite member having a forwardly extending forefoot section;
    an elastomeric sole molded to the underside of the forefoot section of the monolithic composite member, wherein the underside of the elastomeric sole incorporates a predetermined relief pattern; and
    a sole plate having an upper surface with a relief pattern complementary to the relief pattern on the underside of the elastomeric sole, such that the sole plate can be releasably attached to the sole to modify a predetermined parameter of the foot prosthesis' dynamic performance characteristics.

2. A foot prosthesis as defined in claim 1, wherein:
    the elastomeric sole further includes a heel section projecting rearwardly from the forefoot section, to define a heel, and lateral and medial sections projecting laterally from the forefoot section, such that the elastomeric sole has a peripheral shape similar to that of a natural human foot; and
    the sole plate is configured to have a peripheral shape substantially the same as the peripheral shape of the elastomeric sole.

3. A foot prosthesis as defined in claim 2, wherein the sole plate comprises:
    an elongated monolithic composite member extending along the length of the sole plate; and
    a high-density elastomeric member molded around the elongated monolithic composite member;
    wherein the sole plate, when attached to the underside of the elastomeric sole, adjusts the foot prosthesis' stiffness.

4. A foot prosthesis as defined in claim 3, wherein the elongated monolithic composite member extends along substantially the entire length of the sole plate.

5. A foot prosthesis as defined in claim 2, wherein the sole plate is thicker in its rearward portion than in its forward portion, so as to adjust the foot prosthesis' heel height.

6. A foot prosthesis as defined in claim 1, wherein the relief pattern on the underside of the elastomeric sole is a waffle pattern.

7. A foot prosthesis as defined in claim 1, wherein the elongated monolithic composite member has a substantially uniform width.

8. A foot prosthesis as defined in claim 7, wherein the lateral and medial sections of the elastomeric sole have a maximum transverse width about two to three times greater than the substantially uniform width of the composite member.

9. A foot prosthesis as defined in claim 1, wherein:
    the monolithic composite member is formed of a carbon fiber composite material; and
    the elastomeric sole is formed of high-density polyurethane.

10. A foot prosthesis as defined in claim 1, wherein the monolithic composite member further has a generally vertically oriented pylon section that projects above a rearward portion of its forefoot.

11. A foot prosthesis as defined in claim 10, and further comprising an elastomeric coating disposed on the pylon section of the monolithic composite member.

12. A foot prosthesis as defined in claim 1, wherein the prosthesis comprises just a single monolithic composite member.

13. A foot prosthesis as defined in claim 1, and further comprising a low-density foam cosmesis having the general shape of a human foot and configured to conformably envelope the elastomeric sole.

* * * * *